US012140381B2

(12) United States Patent
Yamashita et al.

(10) Patent No.: US 12,140,381 B2
(45) Date of Patent: *Nov. 12, 2024

(54) METHOD FOR PRODUCING A TWO-STAGE HEAT REGENERATING CRYOGENIC REFRIGERATOR

(71) Applicants: Kabushiki Kaisha Toshiba, Tokyo (JP); TOSHIBA MATERIALS CO., LTD., Yokohama (JP)

(72) Inventors: Tomohiro Yamashita, Yokohama (JP); Takahiro Kawamoto, Kawasaki (JP); Tomoko Eguchi, Yokohama (JP); Takashi Kuboki, Ota (JP)

(73) Assignees: Kabushiki Kaisha Toshiba, Tokyo (JP); TOSHIBA MATERIALS CO., LTD., Yokohama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/236,766

(22) Filed: Aug. 22, 2023

(65) Prior Publication Data

US 2023/0408207 A1 Dec. 21, 2023

Related U.S. Application Data

(63) Continuation of application No. 17/728,138, filed on Apr. 25, 2022, now Pat. No. 11,774,184, and a continuation of application No. 16/556,387, filed on Aug. 30, 2019, now Pat. No. 11,346,613.

(30) Foreign Application Priority Data

Mar. 18, 2019 (JP) ................................ 2019-050475

(51) Int. Cl.
*F28D 17/02* (2006.01)
*C09K 5/14* (2006.01)
*F28D 19/04* (2006.01)

(52) U.S. Cl.
CPC ................ *F28D 17/02* (2013.01); *C09K 5/14* (2013.01); *F28D 19/041* (2013.01); *F25B 2309/003* (2013.01)

(58) Field of Classification Search
CPC ......... F28D 17/02; F28D 17/005; C09K 5/14; F25B 2309/003; G01R 33/3804; H01F 6/04
See application file for complete search history.

(56) References Cited

U.S. PATENT DOCUMENTS

| | | | | |
|---|---|---|---|---|
| 7,549,296 | B2 | 8/2009 | Gschneidner et al. | |
| 9,803,895 | B2 | 10/2017 | Xu | |
| 10,101,061 | B2 | 10/2018 | Eguchi et al. | |
| 10,403,423 | B2 | 9/2019 | Ackermann et al. | |
| 11,136,244 | B2 | 10/2021 | Yamada et al. | |
| 11,208,584 | B2 | 12/2021 | Yamashita et al. | |
| 11,774,184 | B2 * | 10/2023 | Yamashita | C09K 5/14 62/3.1 |
| 2002/0031464 | A1 | 3/2002 | Numazawa et al. | |
| 2005/0217280 | A1 | 10/2005 | Gschneidner et al. | |
| 2008/0104967 | A1 | 5/2008 | Satoh | |
| 2012/0157320 | A1 | 6/2012 | Yamada et al. | |
| 2017/0122625 | A1 | 5/2017 | Endo et al. | |
| 2018/0051916 | A1 | 2/2018 | Eguchi et al. | |
| 2021/0309904 | A1 | 10/2021 | Kawamoto et al. | |

FOREIGN PATENT DOCUMENTS

| | | | |
|---|---|---|---|
| JP | 05-171139 | A | 7/1993 |
| JP | 09-324957 | A | 12/1997 |
| JP | 11-264618 | A | 9/1999 |
| JP | 2003-213252 | A | 7/2003 |
| JP | 2005-336240 | A | 12/2005 |
| JP | 2010-064946 | A | 3/2010 |
| JP | 2017-058079 | A | 3/2017 |
| JP | 2018-28045 | A | 2/2018 |
| WO | WO 2011/024757 | A1 | 3/2011 |
| WO | WO 2018/025581 | A1 | 2/2018 |

* cited by examiner

*Primary Examiner* — Jane L Stanley
(74) *Attorney, Agent, or Firm* — Oblon, McClelland, Maier & Neustadt, L.L.P.

(57) ABSTRACT

A method may produce a two-stage heat regenerating cryogenic refrigerator including a vacuum vessel, first and second cylinder disposed in the vessel, the second cylinder coaxially connected to the first cylinder, and first and second regenerator respectively disposed in the first and second cylinder. The method may include: accommodating a first heat regenerating material (HRM) in the first regenerator; and filling a plurality of HRM particles in the second regenerator. The HRM particles may be a second HRM, each of the HRM particles including an oxide or oxysulfide heat regenerating substance having a maximum value of specific heat at a temperature of ≤20 K of 0.3+ $J/cm^3{\cdot}K$ and Ca, Mn, Mg, Be, Sr, Al, Fe, Cu, Ni, and/or Co. Each of the HRM particles may include a first and second region, the second region being closer to an HRM particle outer edge than the first region.

20 Claims, 7 Drawing Sheets

METHOD FOR PRODUCING A TWO-STAGE HEAT REGENERATING CRYOGENIC REFRIGERATOR

CROSS-REFERENCE TO RELATED APPLICATIONS

This application is a continuing application based upon U.S. application Ser. No. 17/728,138, filed on Apr. 25, 2022, and published as US 2022/0243997 A1, which was a continuing application based upon U.S. application Ser. No. 16/556,387, filed Aug. 30, 2019, published as US 2020/0300556 A1 on Sep. 24, 2020, and issued as U.S. Pat. No. 11,346,613 B2, and claims the benefit of priority from Japanese Patent Application No. 2019-050475, filed on Mar. 18, 2019, the entire contents of each of which are incorporated by reference herein.

FIELD

Embodiments described herein relate generally to a heat regenerating material particle, a regenerator, a refrigerator, a superconducting magnet, a nuclear magnetic resonance imaging device, a nuclear magnetic resonance device, a cryopump, and a single-crystal pulling device of a magnetic-field application type.

BACKGROUND

In a cryogenic refrigerator used for a cooling superconducting device, and the like, a heat regenerating material particle containing a heat regenerating substance having high volumetric specific heat in a low-temperature region is used. Here, specific heat per unit volume is defined as volumetric specific heat. As the heat regenerating substance, for example, a metal such as lead (Pb) or bismuth (Bi), a rare earth compound such as $HoCu_2$ or $Er_3Ni$, an oxide such as $Ag_2O$ or $Cu_2O$, or an oxysulfide such as $Gd_2O_2S$ is used.

In a cryogenic refrigerator, the regenerator is filled with a plurality of heat regenerating material particles. For example, the cold is generated by exchanging heat between the heat regenerating material particles and the helium gas passing through the regenerator. The heat regenerating material particles to fill the regenerator are required to have excellent characteristics such as high volumetric specific heat, high mechanical strength, and high heat transfer coefficient.

DETAILED DESCRIPTION

Figure 1A:
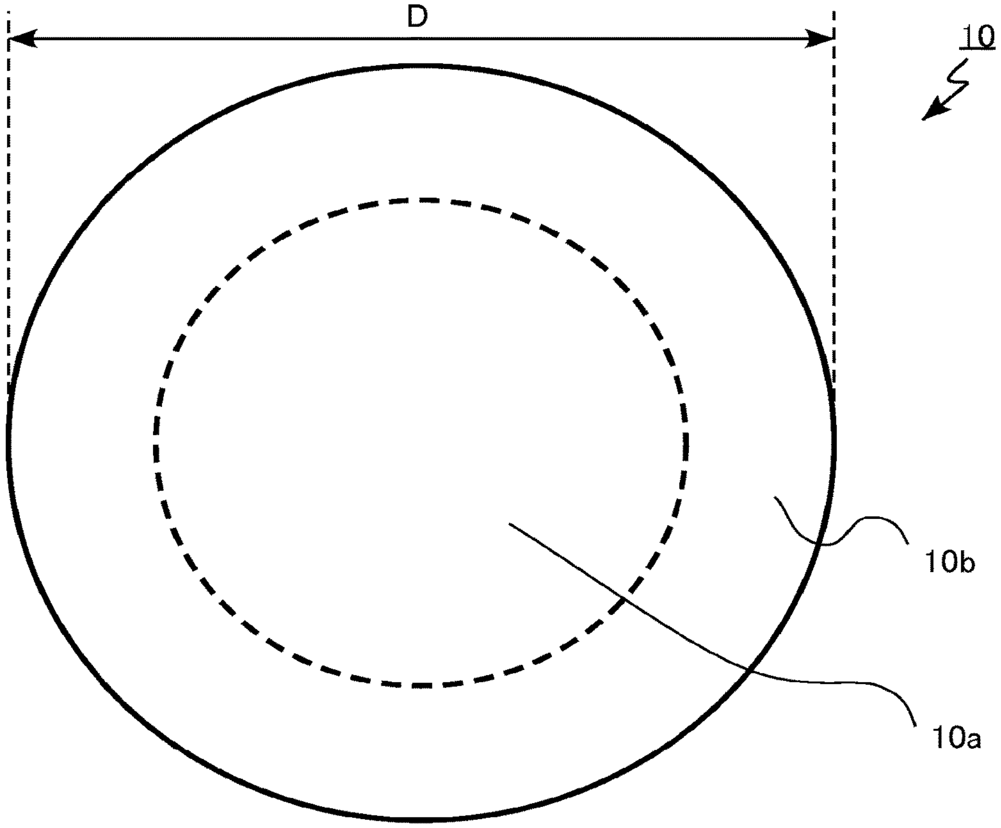
FIGS. 1A and 1B are explanatory drawings of a heat regenerating material particle of a first embodiment.

A heat regenerating material particle of an embodiment contains: a heat regenerating substance having a maximum value of specific heat at a temperature of 20 K or less is 0.3 $J/cm^3 \cdot K$ or more; and one metal element selected from the group consisting of calcium (Ca), magnesium (Mg), beryllium (Be), strontium (Sr), aluminum (Al), iron (Fe), copper (Cu), nickel (Ni), and cobalt (Co), wherein the heat regenerating material particle includes a first region and a second region, the second region is closer to an outer edge of the heat regenerating material particle than the first region, and the second region has a higher concentration of the metal element than the first region.

Hereinafter, embodiments will be described with reference to the drawings. In the following description, the same or similar members are denoted by the same reference numeral, and the description of the member or the like once described may be omitted as appropriate.

In the present specification, a cryogenic temperature means, for example, a temperature range in which the superconducting phenomenon can be used in an industrially useful manner. Such a temperature range is, for example, a temperature range of 20 K or less.

First Embodiment

A heat regenerating material particle of a first embodiment includes a heat regenerating substance having a maximum value of specific heat at a temperature of 20 K or less is 0.3 $J/cm^3 \cdot K$ or more; and one metal element selected from the group consisting of calcium (Ca), magnesium (Mg), beryllium (Be), strontium (Sr), aluminum (Al), iron (Fe), copper (Cu), nickel (Ni), and cobalt (Co). The heat regenerating material particle includes a first region and a second region, the second region is closer to an outer edge of the heat regenerating material particle than the first region, and the second region has a higher concentration of the metal element than the first region.

Figure 1B:
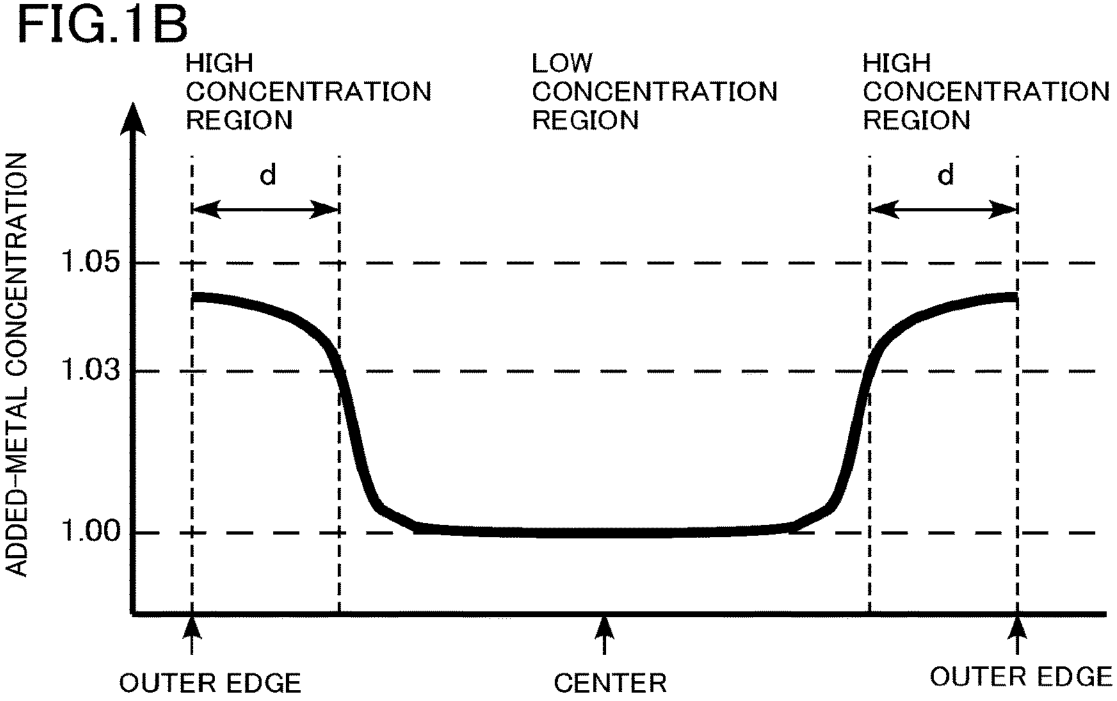

FIGS. 1A and 1B are explanatory diagrams of the heat regenerating material particle of the first embodiment. FIG. 1A is a schematic sectional view of the heat regenerating material particle. FIG. 1B is a view showing a concentration distribution of an added metal in the heat regenerating material particle.

Heat regenerating material particles 10 of the first embodiment are used, for example, in a refrigerator that achieves a cryogenic temperature of 5 K or less.

The shape of the heat regenerating material particle 10 is, for example, spherical. FIGS. 1A and 1B show a case where the heat regenerating material particle 10 is a true sphere. The particle size (D in FIG. 1A) of the heat regenerating material particle is, for example, equal to or more than 50 μm and equal to or less than 500 μm.

The particle size D of the heat regenerating material particle 10 is an equivalent circle diameter. The equivalent circle diameter is the diameter of a perfect circle corresponding to an area of a figure observed in an image such as an optical microscope image or a scanning electron microscope image (SEM image). The particle size D of the heat regenerating material particle 10 can be determined, for example, by image analysis of an optical microscope image or an SEM image.

The heat regenerating material particle 10 contains a heat regenerating substance whose maximum value of specific heat at a temperature of 20 K or less is 0.3 $J/cm^3 \cdot K$ or more.

The heat regenerating substance contains, for example, an oxide. The heat regenerating substance contains, for example, an oxide as the main component. The oxide contained in the heat regenerating substance contains, for example, at least one of silver (Ag) and copper (Cu). The oxide contained in the heat regenerating substance is, for example, silver oxide or copper oxide. The oxide contained in the heat regenerating substance is, for example, $Ag_2O$ or $Cu_2O$.

The heat regenerating substance contains, for example, an oxysulfide. The heat regenerating substance contains, for example, an oxysulfide as the main component. The oxysulfide contained in the heat regenerating substance contains, for example, gadolinium (Gd). The oxysulfide contained in the heat regenerating substance is, for example, gadolinium oxysulfide. The oxysulfide contained in the heat regenerating substance is, for example, $Gd_2O_2S$.

The heat regenerating substance contains, for example, a rare earth compound as the main component. The rare earth compounds contained in the heat regenerating substance are, for example, $HoCu_2$ and $Er_3Ni$.

The composition analysis of the heat regenerating substance can be performed, for example, by energy dispersive X-ray spectroscopy (EDX) or wavelength dispersive X-ray spectrometry (WDX). Moreover, the identification of the heat regenerating substance can be performed by the powder X-ray diffraction method, for example.

The heat regenerating material particle 10 contains an added metal. The added metal is one metal element selected from the group consisting of calcium (Ca), magnesium (Mg), beryllium (Be), strontium (Sr), aluminum (Al), iron (Fe), copper (Cu), nickel (Ni), and cobalt (Co). The added metal is a metal that can be a polyvalent metal ion.

The heat regenerating material particle 10 has a low-concentration region 10*a* (first region) and a high-concentration region 10*b* (second region). The added-metal concentration in the high-concentration region 10*b* is higher than the added-metal concentration in the low-concentration region 10*a*.

The high-concentration region 10*b* is closer to the outer edge of the heat regenerating material particle 10 than the low-concentration region 10*a*. The high-concentration region 10*b* surrounds the low-concentration region 10*a*. The low-concentration region 10*a* is, for example, a region including the center of the heat regenerating material particle 10, and the high-concentration region 10*b* is the outer peripheral region of the low-concentration region 10*a*.

The low-concentration region 10*a* and the high-concentration region 10*b* each contain the heat regenerating substance. At least in the high-concentration region 10*b*, the heat regenerating substance and the added metal are mixed. It is also possible to form a structure where the added metal is not contained in the low-concentration region 10*a*.

The added-metal concentration in the high-concentration region 10*b* is, for example, equal to or more than 0.1 atom % and equal to or less than 2.0 atom %.

The added-metal concentration in the high-concentration region 10*b* is, for example, equal to or more than 1.03 times and equal to or less than 10 times the added-metal concentration in the low-concentration region 10*a*. The distance (d in FIG. 1B) from the outer edge of the heat regenerating material particle 10 in the high-concentration region 10*b*, where the added-metal concentration in the high-concentration region 10*b* is 1.03 times or more the added-metal concentration in the low-concentration region 10*a* is, for example, 1/20 or more of the particle size D of the heat regenerating material particle 10. The distance d may be called a width of the high-concentration region 10*b*. The distance d may be called a distance between the low-concentration region 10*a* and the outer edge of the heat regenerating material particle 10.

The distance (d in FIG. 1B) from the outer edge of the heat regenerating material particle 10 in the high-concentration region 10*b*, where the added-metal concentration is 1.03 times or more the low-concentration region 10*a* is, for example, 10 μm or more.

The added-metal concentration monotonously decreases, for example, from the outer edge of the heat regenerating material particle 10 toward the center.

The detection of the added metal contained in the heat regenerating material particle 10 and the measurement of the added-metal concentration can be performed, for example, by wavelength dispersive X-ray spectrometry (WDX). For example, it is possible to perform: the measurement of the added-metal concentrations at a plurality of locations by WDX from the outer edge of the heat regenerating material particle 10 toward the center; the determination of whether or not the high-concentration region 10*b* close to the outer edge of the heat regenerating material particle 10 exists; the determination of the added-metal concentration in the high-concentration region 10*b*; the calculation of a ratio of the added-metal concentration in the high-concentration region 10*b* to the added-metal concentration in the low-concentration region 10*a*; and the calculation of the distance (d in FIG. 1B) from the outer edge of the heat regenerating material particle 10 in the high-concentration region 10*b* where the added-metal concentration in the high-concentration region 10*b* is 1.03 times or more the added-metal concentration in the low-concentration region 10*a*. Further, for example, the added-metal concentration in the heat regenerating material particle 10 is mapped by WDX, so that it is possible to identify whether or not the high-concentration region 10*b* surrounds the low-concentration region 10*a*.

Next, an example of a method for producing the heat regenerating material particle 10 of the first embodiment will be described.

First, a powder of the heat regenerating substance is added to an aqueous solution of alginic acid and mixed to prepare a slurry. For mixing the powder of the heat regenerating substance and the aqueous solution of alginic acid, for example, a ball mill is used.

The prepared slurry is dropped into a gelling solution to gel the slurry. For dropping the slurry into the gelling solution, for example, a dropper, a burette, a pipette, a syringe, a dispenser, an inkjet, or the like is used. By gelling the slurry, a spherical particle containing a heat regenerating substance are formed in the gelling solution.

The gelling solution contains an ionized added metal. As the time of gelation elapses, the added metal penetrates from the outer edge of the particle toward the center. By controlling the gelation time, the concentration distribution of the added metal in the particle is controlled. That is, by controlling the gelation time, a distribution is formed in which the added-metal concentration in the central region of the particle is low and the added-metal concentration in the outer peripheral region of the particle is high.

From the viewpoint of forming the above distribution, the gelation time is preferably as short as possible, so long as the shape of the particle does not collapse in the subsequent step. The gelation time is preferably within one hour, and more preferably within 30 minutes.

After the formation of the particle by gelation, the particle is washed with pure water. By washing the particle, the added metal adsorbed on the surface of the particle is removed.

After washing the particle, the particle is dried. After the drying of the particle, the particle is sintered to increase the mechanical strength of the particle and the density of the heat regenerating substance in the particle.

The heat regenerating substance is, for example, silver oxide, copper oxide or gadolinium oxysulfide.

The aqueous solution of alginic acid is, for example, an aqueous solution of sodium alginate, an aqueous solution of ammonium alginate, or an aqueous solution of potassium alginate.

The gelling solution is, for example, an aqueous solution of calcium lactate, an aqueous solution of calcium chloride, an aqueous solution of manganese (II) chloride, an aqueous solution of magnesium sulfate, an aqueous solution of beryllium sulfate, an aqueous solution of strontium nitrate, an aqueous solution of aluminum chloride, an aqueous solution of aluminum nitrate, an aqueous solution of aluminum lactate, an aqueous solution of iron chloride (II), an aqueous solution of iron (III) chloride, an aqueous solution of copper (II) chloride, an aqueous solution of nickel (II) chloride, and an aqueous solution of cobalt (II) chloride.

A combination of the heat regenerating substance, the aqueous solution of alginic acid, and the gelling solution is optional. However, when silver oxide as the heat regenerating substance is combined with the aqueous solution of calcium chloride as the gelling solution, silver chloride is generated, and hence this combination is excluded.

The heat regenerating material particle 10 of the first embodiment can be produced by the above production method.

Next, the function and effects of the heat regenerating material particle 10 of the first embodiment will be described.

In a cryogenic refrigerator used for cooling a superconducting device and for other purposes, a regenerator is filled with a plurality of heat regenerating material particles. For example, the cold is generated by exchanging heat between the heat regenerating material particles and the helium gas passing through the regenerator. The heat regenerating material particles to fill the regenerator are required to have excellent characteristics such as high volumetric specific heat, high mechanical strength, and high thermal conductivity.

The heat regenerating material particle 10 of the first embodiment contains a heat regenerating substance whose maximum value of specific heat at a temperature of 20 K or less is 0.3 $J/cm^3 \cdot K$ or more. Therefore, the heat regenerating material particle 10 has high volumetric specific heat at a cryogenic temperature.

Moreover, the heat regenerating material particle 10 of the first embodiment includes a high-concentration region 10*b* having a high added-metal concentration in the outer peripheral region of the particle. The added metal has a function of promoting sintering of the particle at the time of sintering during production of the heat regenerating material particle 10. Therefore, the high-concentration region 10*b* has a high degree of sintering and high mechanical strength. Hence the heat regenerating material particle 10 has high mechanical strength.

Further, due to the high degree of sintering of the high-concentration region 10*b*, the thermal conductivity of the high-concentration region 10*b* is high. Therefore, the heat regenerating material particle 10 has high thermal conductivity.

When the added-metal concentration increases, the volume ratio of the added metal increases while the degree of sintering of the particle increases, thereby causing a problem where the volume ratio of the heat regenerating substance decreases. In addition, the added metal forms a compound having low specific heat by reaction with the heat regenerating substance. Thus, when the added-metal concentration becomes high, the heat regenerating substance changes into a compound having low specific heat, thereby causing a problem where the volume ratio of the heat regenerating substance decreases.

The heat regenerating material particle 10 of the first embodiment includes the low-concentration region 10*a* having a low added-metal concentration in the central region of the particle. Therefore, in the central region of the particle, the decrease in the volume ratio of the heat regenerating substance due to the added element is reduced. Hence the heat regenerating material particle 10 has high volumetric specific heat.

In the heat regenerating material particle 10 of the first embodiment, the mechanical strength and the thermal conductivity are improved by providing the high-concentration region 10*b* having a high added-metal concentration in the outer peripheral region of the particle. On the other hand, the volumetric specific heat is improved by providing the low-concentration region 10*a* in the central region of the particle. The heat regenerating material particle 10 of the first embodiment has high volumetric specific heat, high mechanical strength, and high thermal conductivity by optimizing the concentration distribution of the added element in the particle.

The optimization of the concentration distribution of the added element in the heat regenerating material particles 10 can be achieved by optimizing the gelation time during production of the heat regenerating material particle 10. More specifically, the optimization can be achieved by shortening the gelation time as much as possible. When the gelation time is excessively long, the concentration of the added element in the heat regenerating material particle 10 becomes uniform to cause deterioration in characteristics. The gelation time is preferably within one hour, and more preferably within 30 minutes.

From the viewpoint of increasing the mechanical strength and the thermal conductivity of the heat regenerating material particle 10, the added-metal concentration in the high-concentration region 10*b* is preferably 0.1 atom % or more, and more preferably 0.2 atom % or more.

From the viewpoint of achieving high mechanical strength, high thermal conductivity, and high volumetric specific heat of the heat regenerating material particle 10, the added-metal concentration in high-concentration region 10*b* is 1.03 times or more the added-metal concentration in low-concentration region 10*a*, more preferably 1.05 times or more, further preferably 1.1 times or more, and most preferably 1.2 times or more.

From the viewpoint of increasing the mechanical strength and the thermal conductivity of the heat regenerating material particle 10, the distance (d in FIG. 1B) from the outer edge of the heat regenerating material particle 10 in the high-concentration region 10*b*, where the added-metal concentration in the high-concentration region 10*b* is 1.03 times or more the added-metal concentration in the low-concentration region 10*a* is preferably 1/20 or more of the particle size D (D in FIG. 1A) of the heat regenerating material particle 10, and more preferably 1/10 or more of the particle size D.

From the viewpoint of increasing the mechanical strength and the thermal conductivity of the heat regenerating material particle 10, the distance from the outer edge of the heat regenerating material particle 10 in the high-concentration region 10*b* where the added-metal concentration is 1.1 times or more the added-metal concentration (d in FIG. 1B) is preferably 10 μm or more, and more preferably 20 μm or more.

From the viewpoint of achieving high mechanical strength, high thermal conductivity, and high volumetric specific heat of the heat regenerating material particle 10, the added-metal concentration preferably decreases monotonously from the outer edge of the heat regenerating material particle 10 toward the center.

From the viewpoint of increasing the mechanical strength and the thermal conductivity of the heat regenerating material particle 10, the added element is preferably calcium (Ca) having a high ability to promote sintering.

Hereinafter, examples and comparative examples of the heat regenerating material particle 10 of the first embodiment and evaluation results of those will be described.

According to the method for producing a heat regenerating material particle of the first embodiment described above, a heat regenerating material particle was produced. Silver oxide, copper oxide, and gadolinium oxysulfide were used as a heat regenerating substance, an aqueous solution of sodium alginate was used as an aqueous solution of alginic acid, an aqueous solution of calcium lactate was used as a gelling solution, and a syringe was used as a dropping method. The concentration of the aqueous solution of sodium alginate, the amount of the heat regenerating substance to be added to the aqueous solution of sodium alginate, the concentration of the aqueous solution of calcium lactate, and the gelation time were appropriately changed to obtain heat regenerating material particles shown in Table 1 (Examples 1 to 18, Comparative Example 1 to 3).

In order to evaluate the mechanical strength required of heat regenerating material particles when the regenerator constituting the refrigerator is filled with the heat regenerating material particles and the refrigerator operates, each cylindrical container having a diameter of φ 15 mm and a height of 5 cm is filled with the produced heat regenerating material particles, and a single vibration with a maximum acceleration of 200 $m/s^2$ was applied to the container 1,000 times. The presence or absence of a broken heat regenerating material particle as a result of the above is shown. It can be seen that when the concentration (atom %) of the metal element in the second region falls below 0.1, the sintering does not proceed sufficiently and the mechanical strength of the heat regenerating material particle decreases.

In addition, the volumetric specific heat at 20 K is measured and compared with the volumetric specific heat inherent to the heat regenerating substance, that is, the volumetric specific heat at the time when the heat regenerating substance volume ratio is 100 vol %, to evaluate the volumetric specific heat reduction rate of the heat regenerating material particles obtained this time (Examples 1 to 18 and Comparative Examples 1 to 3) with respect to the volumetric specific heat at the time when the heat regenerating substance volume ratio is 100 vol %. From this result, when the concentration ratio (C2/C1) of the concentration (C2) of the metal element in the second region to the concentration (C1) of the metal element in the first region falls below 1.03, the metal element extends throughout the heat regenerating material particle and the ratio of the metal element becomes excessive, so that a decrease in volumetric specific heat is observed. Then, it is found that, when the concentration ratio becomes 1, that is, when the concentration (C1) of the metal element in the first region and the concentration (C2) of the metal element in the second region become equal, a decrease in volumetric specific heat exceeds 5% which is not preferred in practical use.

TABLE 1

| | Cold accumulating substance | Conc. (C1) of metal element in first region | Conc. (C2) of metal element in second region | Conc. ration (C2/C1) | Destructive particle | Specific heat reduction rate @20 K |
|---|---|---|---|---|---|---|
| Example 1 | Silver oxide | 0.126% | 0.130% | 1.03 | No | less than 1% |
| Example 2 | Silver oxide | 0.147% | 0.154% | 1.05 | No | less than 1% |
| Example 3 | Silver oxide | 0.193% | 0.212% | 1.1 | No | less than 1% |
| Example 4 | Silver oxide | 0.100% | 0.102% | 1.02 | No | 2% |
| Example 5 | Silver oxide | 0.229% | 0.231% | 1.01 | No | 4% |
| Example 6 | Silver oxide | 0.060% | 0.063% | 1.05 | Yes | less than 1% |
| Comparative Example 1 | Silver oxide | 0.125% | 0.125% | 1 | No | 6% |
| Example 7 | Copper oxide | 0.127% | 0.131% | 1.03 | No | less than 1% |
| Example 8 | Copper oxide | 0.107% | 0.112% | 1.05 | No | less than 1% |
| Example 9 | Copper oxide | 0.066% | 0.069% | 1.05 | Yes | less than 1% |
| Example 10 | Copper oxide | 0.106% | 0.108% | 1.02 | No | 2% |
| Example 11 | Copper oxide | 0.143% | 0.144% | 1.01 | No | 4% |
| Example 12 | Copper oxide | 0.145% | 0.159% | 1.1 | No | less than 1% |
| Comparative Example 2 | Copper oxide | 0.138% | 0.138% | 1 | No | 6% |
| Example 13 | Gadolinium | 0.191% | 0.197% | 1.03 | No | less than |

TABLE 1-continued

| | Cold accumulating substance | Conc. (C1) of metal element in first region | Conc. (C2) of metal element in second region | Conc. ration (C2/C1) | Destructive particle | Specific heat reduction rate @20 K |
|---|---|---|---|---|---|---|
| | oxysulfide | | | | | 1% |
| Example 14 | Gadolinium oxysulfide | 0.230% | 0.242% | 1.05 | No | less than 1% |
| Example 15 | Gadolinium oxysulfide | 0.179% | 0.197% | 1.1 | No | less than 1% |
| Example 16 | Gadolinium oxysulfide | 0.184% | 0.188% | 1.02 | No | 2% |
| Example 17 | Gadolinium oxysulfide | 0.128% | 0.129% | 1.01 | No | 4% |
| Example 18 | Gadolinium oxysulfide | 0.052% | 0.055% | 1.05 | Yes | less than 1% |
| Comparative Example 3 | Gadolinium oxysulfide | 0.135% | 0.135% | 1 | No | 6% |

As described above, of the first embodiment, it is possible to achieve a heat regenerating material particle having excellent characteristics such as high volumetric specific heat, high mechanical strength, and a high heat transfer coefficient.

Second Embodiment

A refrigerator of a second embodiment is a refrigerator including a regenerator filled with a plurality of heat regenerating material particles of the first embodiment. Hereinafter, a part of the description of contents overlapping with those of the first embodiment will be omitted.

Figure 2:
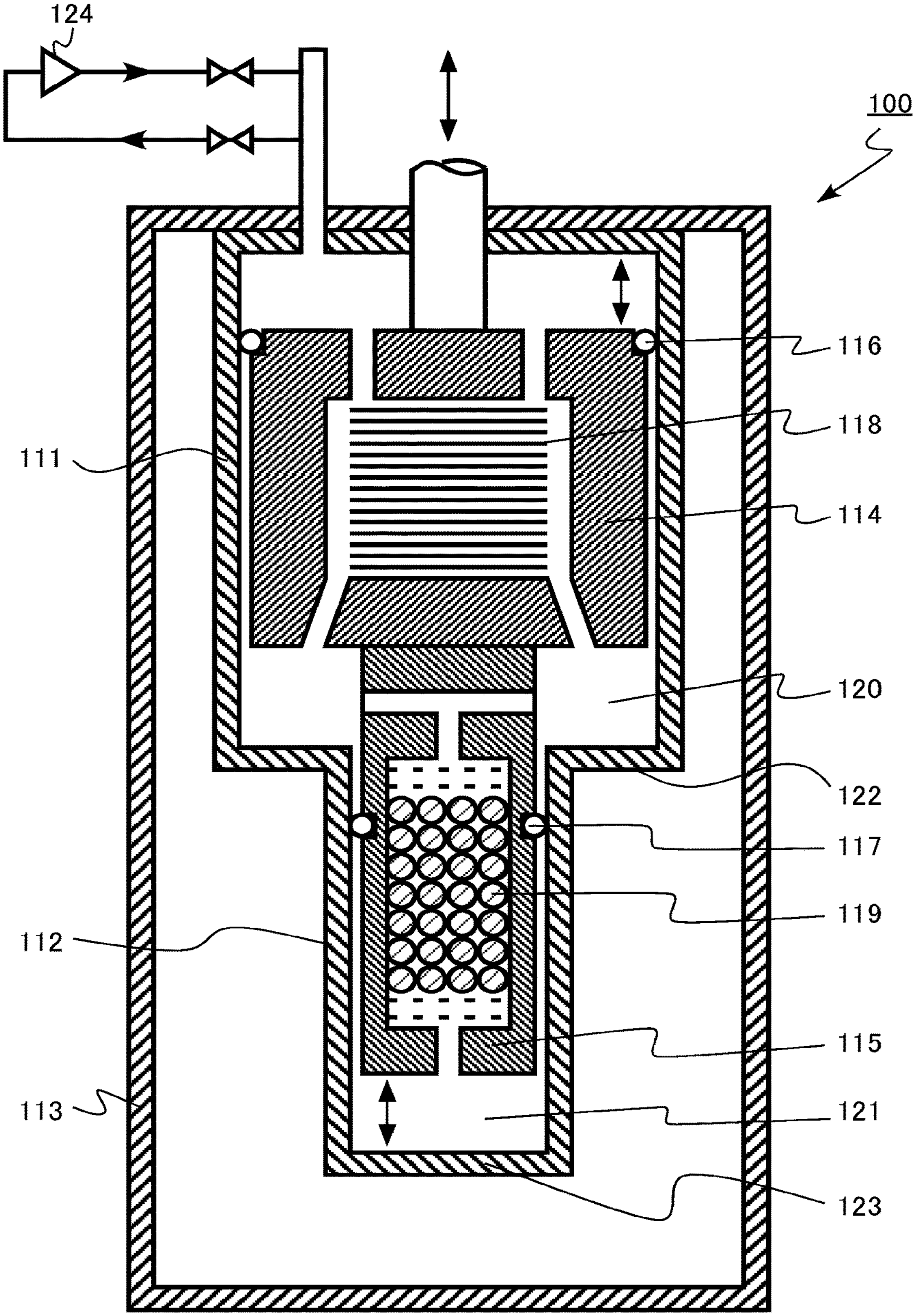
FIG. 2 is a schematic sectional view showing a main-part configuration of a refrigerator of a second embodiment.

FIG. 2 is a schematic sectional view showing a main-part configuration of the refrigerator of the second embodiment. The refrigerator of the second embodiment is a two-stage heat regenerating cryogenic refrigerator 100 used for cooling a superconducting device or the like.

The heat regenerating cryogenic refrigerator 100 includes a first cylinder 111, a second cylinder 112, a vacuum vessel 113, a first regenerator 114, a second regenerator 115, a first seal ring 116, a second seal ring 117, a first heat regenerating material 118, a second heat regenerating material 119, a first expansion chamber 120, a second expansion chamber 121, a first cooling stage 122, a second cooling stage 123, and a compressor 124.

The heat regenerating cryogenic refrigerator 100 includes a vacuum vessel 113 in which the first cylinder 111 having a large diameter and the second cylinder 112 having a small diameter and coaxially connected to the first cylinder 111 are installed. The first regenerator 114 is disposed in the first cylinder 111 so as to be able to reciprocate. In the second cylinder 112, the second regenerator 115 which is an example of the regenerator of the second embodiment is disposed so as to be able to reciprocate.

A first seal ring 116 is disposed between the first cylinder 111 and the first regenerator 114. A second seal ring 117 is disposed between the second cylinder 112 and the second regenerator 115.

The first regenerator 114 accommodates a first heat regenerating material 118 such as a Cu mesh. The second regenerator 115 is filled with a plurality of heat regenerating material particles 10 of the first embodiment as the second heat regenerating material 119.

The first regenerator 114 and the second regenerator 115 each have a passage of a working medium provided in a gap between the first heat regenerating material 118 and the second heat regenerating material 119, or the like. The working medium is helium gas.

The first expansion chamber 120 is provided between the first regenerator 114 and the second regenerator 115. Further, the second expansion chamber 121 is provided between the second regenerator 115 and the end wall of the second cylinder 112. The first cooling stage 122 is provided at the bottom of the first expansion chamber 120. In addition, the second cooling stage 123 having a temperature lower than that of the first cooling stage 122 is formed at the bottom of the second expansion chamber 121.

The first expansion chamber 120 is provided between the first regenerator 114 and the second regenerator 115. Further, the second expansion chamber 121 is provided between the second regenerator 115 and the end wall of the second cylinder 112. The first cooling stage 122 is provided at the bottom of the first expansion chamber 120. In addition, the second cooling stage 123 having a temperature lower than that of the first cooling stage 122 is formed at the bottom of the second expansion chamber 121.

A high-pressure working medium is supplied from the compressor 124 to the above-described two-stage heat regenerating cryogenic refrigerator 100. The supplied working medium passes through the first heat regenerating material 118 accommodated in the first regenerator 114 and reaches the first expansion chamber 120. The supplied working medium then passes through the second heat regenerating material 119 accommodated in the second regenerator 115 and reaches the second expansion chamber 121.

At this time, the working medium is cooled by supplying thermal energy to the first heat regenerating material 118 and the second heat regenerating material 119. The working medium having passed through the first heat regenerating material 118 and the second heat regenerating material 119 is expanded in the first expansion chamber 120 and the second expansion chamber 121 to generate the cold. Then, the first cooling stage 122 and the second cooling stage 123 are cooled.

The expanded working medium flows in the opposite direction through the first heat regenerating material 118 and the second heat regenerating material 119. The working medium is discharged after receiving thermal energy from the first heat regenerating material 118 and the second heat regenerating material 119. The heat regenerating cryogenic refrigerator 100 is configured such that in such a process as above, as the heat recovery effect becomes better, the thermal efficiency of the working medium cycle is improved, and a lower temperature is achieved.

As described above, according to the second embodiment, a refrigerator with excellent characteristics can be achieved by using the heat regenerating material particles with excellent characteristics.

Third Embodiment

A superconducting magnet of a third embodiment includes the refrigerator of the second embodiment. Hereinafter, a part of the description of contents overlapping with those of the second embodiment will be omitted.

Figure 3:
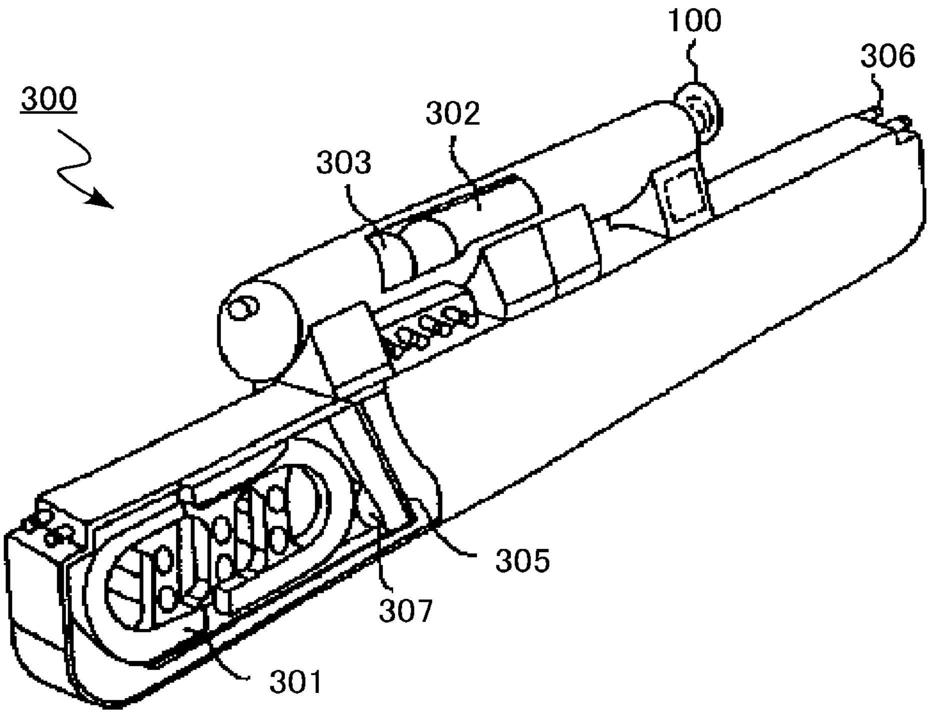
FIG. 3 is a perspective view showing a schematic configuration of a superconducting magnet of a third embodiment.

FIG. 3 is a perspective view showing a schematic configuration of the superconducting magnet of the third embodiment. The superconducting magnet of the third embodiment is a superconducting magnet 300 for a magnetically levitated train which includes the heat regenerating cryogenic refrigerator 100 of the second embodiment.

The superconducting magnet 300 for a magnetically levitated train includes a superconducting coil 301, a liquid helium tank 302 for cooling the superconducting coil 301, a liquid nitrogen tank 303 for preventing volatilization of the liquid helium tank 302, a laminated heat insulating material 305, a power lead 306, a permanent current switch 307, and the heat regenerating cryogenic refrigerator 100.

According to the third embodiment, a superconducting magnet with excellent characteristics can be achieved by using the refrigerator with excellent characteristics.

Fourth Embodiment

A nuclear magnetic resonance imaging device of a fourth embodiment includes the refrigerator of the second embodiment. Hereinafter, a part of the description of contents overlapping with those of the second embodiment will be omitted.

Figure 4:
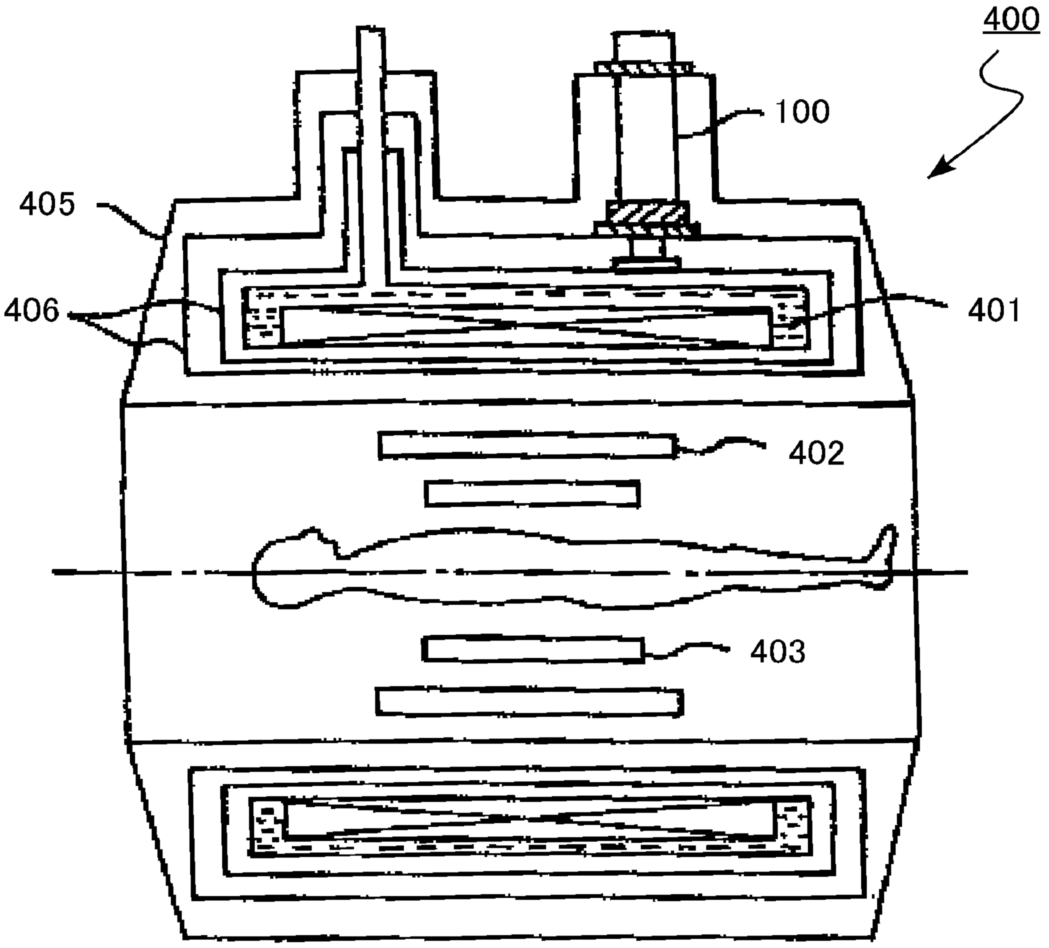
FIG. 4 is a sectional view showing a schematic configuration of a nuclear magnetic resonance imaging device of a fourth embodiment.

FIG. 4 is a sectional view showing a schematic configuration of the nuclear magnetic resonance imaging device of the fourth embodiment. The nuclear magnetic resonance imaging (MRI) device of the fourth embodiment is a nuclear magnetic resonance imaging device 400 including the heat regenerating cryogenic refrigerator 100 of the second embodiment.

The nuclear magnetic resonance imaging device 400 includes a superconducting static magnetic field coil 401 for applying a spatially uniform and temporally stable static magnetic field to a human body, a correction coil (not shown) for correcting nonuniformity of a generated magnetic field, a gradient magnetic field coil 402 for giving a magnetic field gradient to a measurement region, a radio wave transmitting/receiving probe 403, a cryostat 405, and a radiation adiabatic shield 406. The heat regenerating cryogenic refrigerator 100 is used for cooling the superconducting static magnetic field coil 401.

According to the fourth embodiment, a nuclear magnetic resonance imaging device with excellent characteristics can be achieved by using the refrigerator with excellent characteristics.

Fifth Embodiment

A nuclear magnetic resonance device of a fifth embodiment includes the refrigerator of the second embodiment. Hereinafter, a part of the description of contents overlapping with those of the second embodiment will be omitted.

Figure 5:
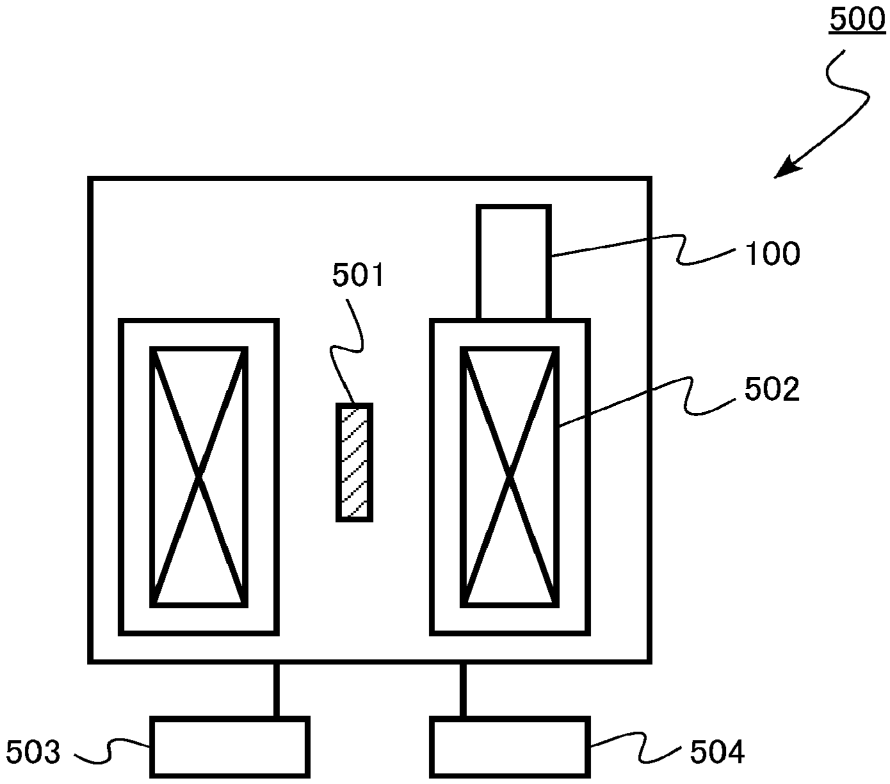
FIG. 5 is a sectional view showing a schematic configuration of a nuclear magnetic resonance device of a fifth embodiment.

FIG. 5 is a sectional view showing a schematic configuration of the nuclear magnetic resonance device of the fifth embodiment. The nuclear magnetic resonance (NMR) device of the fifth embodiment is a nuclear magnetic resonance device 500 including the heat regenerating cryogenic refrigerator 100 of the second embodiment.

The nuclear magnetic resonance device 500 includes a superconducting static magnetic field coil 502 for applying a magnetic field to a sample such as an organic substance contained in a sample tube 501, a high-frequency oscillator 503 for applying a radio wave to the sample tube 501 in the magnetic field, and an amplifier 504 for amplifying an induced current generated in a coil (not shown) on the periphery of the sample tube 501. In addition, the heat regenerating cryogenic refrigerator 100 for cooling the superconducting static magnetic field coil 502 is provided.

According to the fifth embodiment, a nuclear magnetic resonance device with excellent characteristics can be achieved by using the refrigerator with excellent characteristics.

Sixth Embodiment

A cryopump of a sixth embodiment includes the refrigerator of the second embodiment. Hereinafter, a part of the description of contents overlapping with those of the second embodiment will be omitted.

Figure 6:
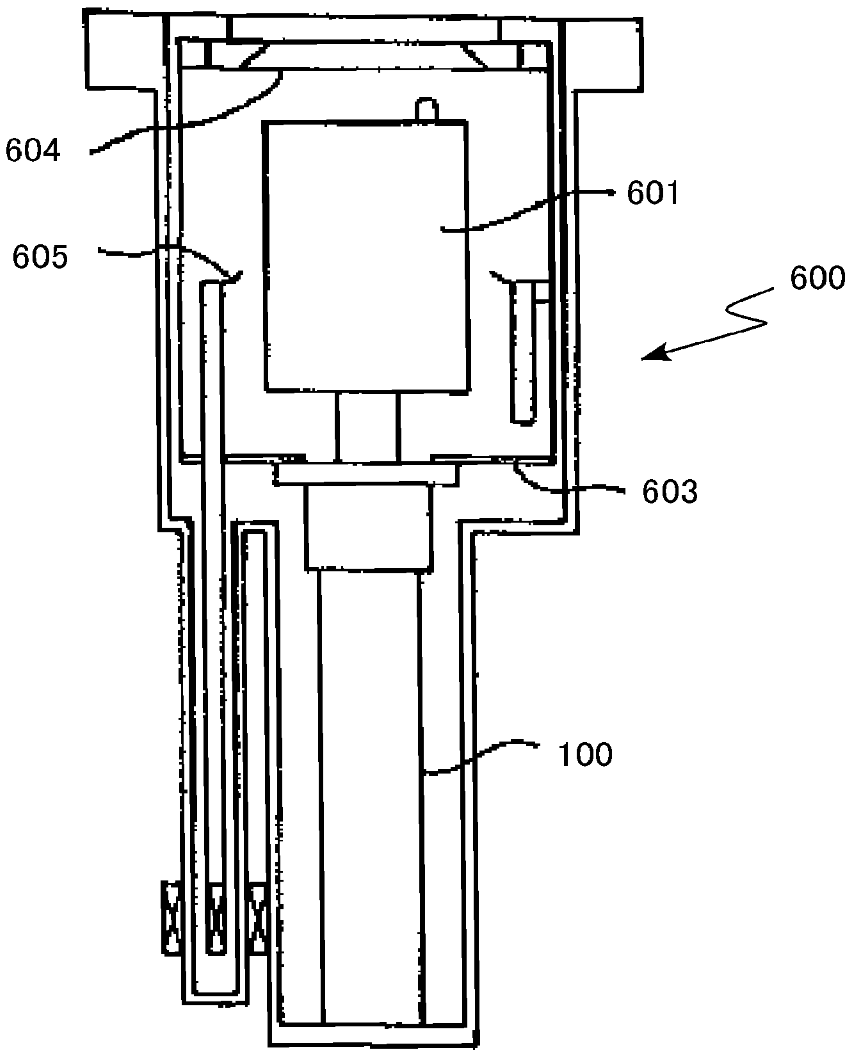
FIG. 6 is a sectional view showing a schematic configuration of a cryopump of a sixth embodiment.

FIG. 6 is a sectional view showing a schematic configuration of the cryopump of the sixth embodiment. The cryopump of the sixth embodiment is a cryopump 600 including the heat regenerating cryogenic refrigerator 100 of the second embodiment.

The cryopump 600 includes a cryopanel 601 for condensing or adsorbing gas molecules, the heat regenerating cryogenic refrigerator 100 for cooling the cryopanel 601 to a predetermined cryogenic temperature, a shield 603 provided between the cryopanel 601 and the heat regenerating cryogenic refrigerator 100, a baffle 604 provided at an inlet port, and a ring 605 for changing an exhaust rate of argon, nitrogen, hydrogen, or the like.

According to the sixth embodiment, a cryopump with excellent characteristics can be achieved by using the refrigerator with excellent characteristics.

Seventh Embodiment

A single-crystal pulling device of a magnetic-field application type of a seventh embodiment includes the refrigerator of the second embodiment. Hereinafter, a part of the description of contents overlapping with those of the second embodiment will be omitted.

Figure 7:
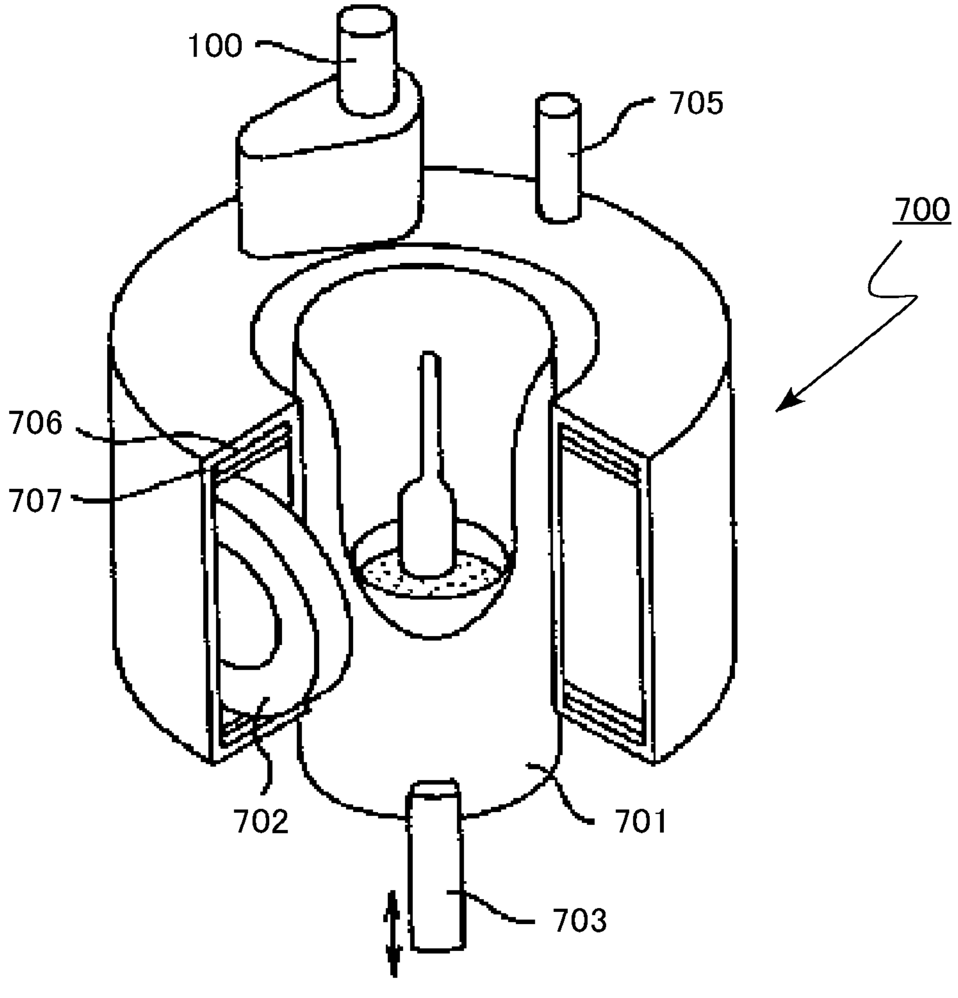
FIG. 7 is a perspective view showing a schematic configuration of a single-crystal pulling device of a magnetic-field application type of a seventh embodiment.

FIG. 7 is a perspective view showing a schematic configuration of the single-crystal pulling device of the magnetic-field application type of the seventh embodiment. The single-crystal pulling device of the magnetic-field application type of the seventh embodiment is a single-crystal pulling device 700 of a magnetic-field application type including the heat regenerating cryogenic refrigerator 100 of the second embodiment.

The single-crystal pulling device 700 of the magnetic-field application type includes a single-crystal pulling unit 701 having a raw-material melting crucible, a heater, a single-crystal pulling mechanism, and the like, a superconducting coil 702 for applying a static magnetic field to a raw material melt, a lifting mechanism 703 of the single-crystal pulling unit 701, a current lead 705, a heat shield plate 706, and a helium container 707. The heat regenerating cryogenic refrigerator 100 is used for cooling the superconducting coil 702.

According to the seventh embodiment, a single-crystal pulling device of a magnetic-field application type with excellent characteristics can be achieved by using the refrigerator with excellent characteristics.

While certain embodiments have been described, these embodiments have been presented by way of example only, and are not intended to limit the scope of the inventions. Indeed, the heat regenerating material particle, the regenerator, the refrigerator, the superconducting magnet, the nuclear magnetic resonance imaging device, the nuclear magnetic resonance device, the cryopump, and the single-crystal pulling device of the magnetic-field application type described herein may be embodied in a variety of other forms; furthermore, various omissions, substitutions and changes in the form of the devices and methods described herein may be made without departing from the spirit of the inventions. The accompanying claims and their equivalents are intended to cover such forms or modifications as would fall within the scope and spirit of the inventions.

What is claimed is:

1. A method for producing a two-stage heat regenerating cryogenic refrigerator, the two-stage heat regenerating cryogenic refrigerator including a vacuum vessel, a first cylinder disposed in the vessel, a second cylinder disposed in the vessel and coaxially connected to the first cylinder, a first regenerator disposed in the first cylinder, and a second regenerator disposed in the second cylinder, the method comprising:

accommodating a first heat regenerating material in the first regenerator; and filling a plurality of heat regenerating material particles in the second regenerator, the heat regenerating material particles being a second heat regenerating material, each of the heat regenerating material particles including a heat regenerating substance having a maximum value of specific heat at a temperature of 20 K or less of 0.3 $J/cm^3 \cdot K$ or more and one metal element selected from the group consisting of calcium (Ca), manganese (Mn), magnesium (Mg), beryllium (Be), strontium (Sr), aluminum (Al), iron (Fe), copper (Cu), nickel (Ni), and cobalt (Co), wherein each of the heat regenerating material particles includes a first region and a second region, wherein the second region is closer to an outer edge of each of the heat regenerating material particles than the first region, wherein the second region has a higher concentration of the metal element than the first region, wherein the first region and the second region contain the heat regenerating substance, and wherein the heat regenerating substance comprises a component in a form of an oxide or an oxysulfide.

2. The method of claim 1, wherein the second cylinder has a diameter smaller than a diameter of the first cylinder.

3. The method of claim 1, wherein the first heat regenerating material is a Cu mesh.

4. The method of claim 1, wherein the second region surrounds the first region.

5. The method of claim 1, wherein a concentration of the metal element in the second region is 0.1 atom % or more.

6. The method of claim 1, wherein a concentration of the metal element in the second region is 1.03 times or more a concentration of the metal element in the first region.

7. The method of claim 6, wherein a distance from the outer edge of each of the heat regenerating material particles in the second region is 1/20 or more of a particle size of each of the heat regenerating material particles.

8. The method of claim 6, wherein a distance from the outer edge of each of the heat regenerating material particles in the second region is 10 μm or more.

9. The method of claim 1, wherein a concentration of the metal element monotonously decreases from the outer edge of each of the heat regenerating material particles toward a center of each of the heat regenerating material particles.

10. The method of claim 1, wherein a particle size of each of the heat regenerating material particles is equal to or more than 50 μm and equal to or less than 500 μm.

11. The method of claim 1, wherein the heat regenerating substance comprises a component in a form of silver oxide, copper oxide, or gadolinium oxysulfide.

12. A method for producing a two-stage heat regenerating cryogenic refrigerator, the two-stage heat regenerating cryogenic refrigerator including a vacuum vessel, a first cylinder disposed in the vessel, a second cylinder disposed in the vessel and coaxially connected to the first cylinder, a first regenerator disposed in the first cylinder, and a second regenerator disposed in the second cylinder, the method comprising:

accommodating a first heat regenerating material in the first regenerator; and filling a plurality of heat regenerating material particles in the second regenerator, the heat regenerating material particles being a second heat regenerating material, each of the heat regenerating material particles including a heat regenerating substance having a maximum value of specific heat at a temperature of 20 K or less of 0.3 $J/cm^3 \cdot K$ or more and one metal element selected from the group consisting of calcium (Ca), manganese (Mn), magnesium (Mg), beryllium (Be), strontium (Sr), aluminum (Al), iron (Fe), nickel (Ni), and cobalt (Co), wherein each of the heat regenerating material particles comprises a first region and a second region, wherein the second region is closer to an outer edge of each of the heat regenerating material particles than the first region, and wherein the second region has a higher concentration of the metal element than the first region.

13. The method of claim 12, wherein the second cylinder has a diameter smaller than a diameter of the first cylinder.

14. The method of claim 12, wherein the first heat regenerating material is a Cu mesh.

15. The method of claim 12, wherein the heat regenerating substance comprises a component in a form of an oxide or an oxysulfide.

16. The method of claim 12, wherein the heat regenerating substance comprises a component in a form of silver oxide, copper oxide, or gadolinium oxysulfide.

17. The method of claim 12, wherein the second region surrounds the first region.

18. The method of claim 12, wherein a concentration of the metal element in the second region is 0.1 atom % or more.

19. The method of claim 12, wherein a concentration of the metal element in the second region is 1.03 times or more a concentration of the metal element in the first region.

20. The method of claim 19, wherein a distance from the outer edge of each of the heat regenerating material particles in the second region is 1/20 or more of a particle size of each of the heat regenerating material particles.

* * * * *